(12) United States Patent
Dijkstra

(10) Patent No.: US 7,966,860 B2
(45) Date of Patent: Jun. 28, 2011

(54) METHOD FOR CONFIGURING AN ARRAY OF TRANSDUCERS IN AN ULTRASONIC TEST APPARATUS

(75) Inventor: Frederik Hendrik Dijkstra, Oudenbosch (NL)

(73) Assignee: Röntgen Technische Dienst B.V., NC Rotterdam (NL)

( * ) Notice: Subject to any disclaimer, the term of this patent is extended or adjusted under 35 U.S.C. 154(b) by 589 days.

(21) Appl. No.: 11/992,757

(22) PCT Filed: Dec. 3, 2007

(86) PCT No.: PCT/NL2007/050612
§ 371 (c)(1),
(2), (4) Date: Mar. 28, 2008

(87) PCT Pub. No.: WO2008/075943
PCT Pub. Date: Jun. 26, 2008

(65) Prior Publication Data
US 2010/0218589 A1 Sep. 2, 2010

Related U.S. Application Data

(60) Provisional application No. 60/861,964, filed on Dec. 1, 2006.

(51) Int. Cl.
*G01N 29/30* (2006.01)
(52) U.S. Cl. .......... 73/1.86; 73/1.82
(58) Field of Classification Search .......... 73/1.82, 73/1.86
See application file for complete search history.

(56) References Cited

U.S. PATENT DOCUMENTS

| 4,106,326 | A | * | 8/1978 | Lather et al. | 73/1.86 |
| 4,393,711 | A | * | 7/1983 | Lapides | 73/592 |
| 4,462,082 | A | * | 7/1984 | Thiele et al. | 702/103 |
| 6,405,596 | B1 | * | 6/2002 | Kruzic | 73/611 |

(Continued)

FOREIGN PATENT DOCUMENTS

EP 0 217 783 4/1987

(Continued)

OTHER PUBLICATIONS

International Search Report dated Jun. 27, 2008.

(Continued)

*Primary Examiner* — Hezron Williams
*Assistant Examiner* — Rose M Miller
(74) *Attorney, Agent, or Firm* — Jacobson Holman PLLC

(57) ABSTRACT

A method for configuring an array of transducers in an ultrasonic test apparatus for detecting flaws in welds connecting the edges of metal bodies such as plates or pipelines. The method includes the steps of: providing geometrical data of the bevelled edges of the bodies before being welded; identifying different facets of the geometry of the edges; providing geometrical data of a reference plate including a reflector; selecting the angles; and the positions of the transducers in accordance with the geometry of the edges; mounting the transducers to a scanning mechanism in accordance with the selections made; connecting the transducers to at least one control unit for transmitting ultrasound and receiving echo signals by means of the transducers and subsequently calibrating by means of the reference plate the positions of the transducers relative to the scanning mechanism and calibrating gain and gate settings by means of the reference plate.

21 Claims, 10 Drawing Sheets

U.S. PATENT DOCUMENTS

| | | | |
|---|---|---|---|
| 7,278,289 B2 * | 10/2007 | Gessert et al. | 73/1.82 |
| 2009/0178465 A1 * | 7/2009 | Ethridge et al. | 73/1.82 |
| 2009/0178466 A1 * | 7/2009 | Ethridge et al. | 73/1.86 |
| 2010/0107725 A1 * | 5/2010 | Iizuka et al. | 73/1.82 |

FOREIGN PATENT DOCUMENTS

| | | |
|---|---|---|
| WO | WO 02/31487 | 4/2002 |
| WO | WO 2004/097397 | 11/2004 |

OTHER PUBLICATIONS

Dijkstra, F.H., "*Characterization of probes used for periodic inspection*" Ultrasonic Materials Characterization. Proceedings of the First International Symposium on Ultrasonic Materils Characterization, pp. 605-615 (Jun. 7-9, 1978).

API 620, $10^{th}$ Edition Feb. 2002 (with addendum Jun. 2004).

Handbook on Ultrasonic Examination of Austenitic Welds (1986).

* cited by examiner

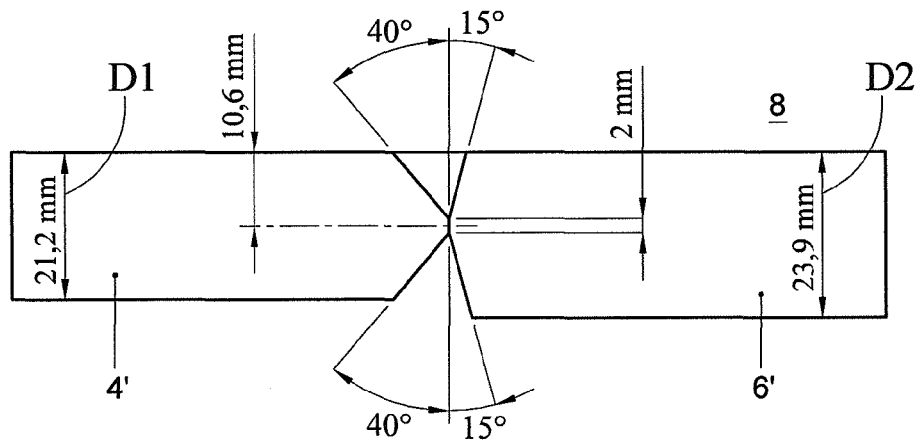
Fig. 3.1
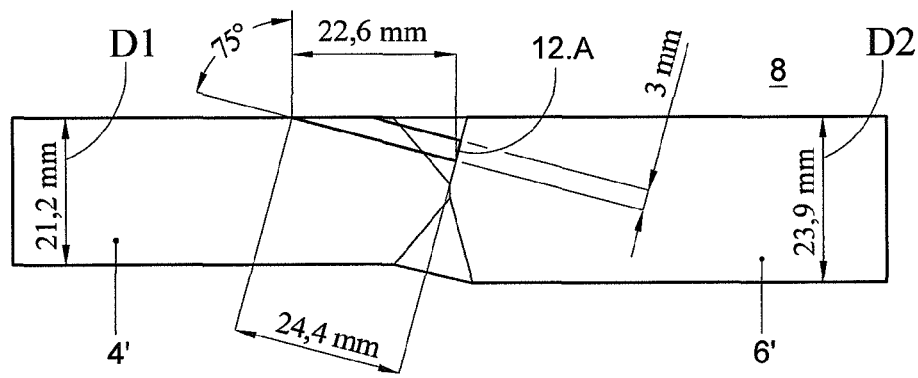
Fig. 3.2
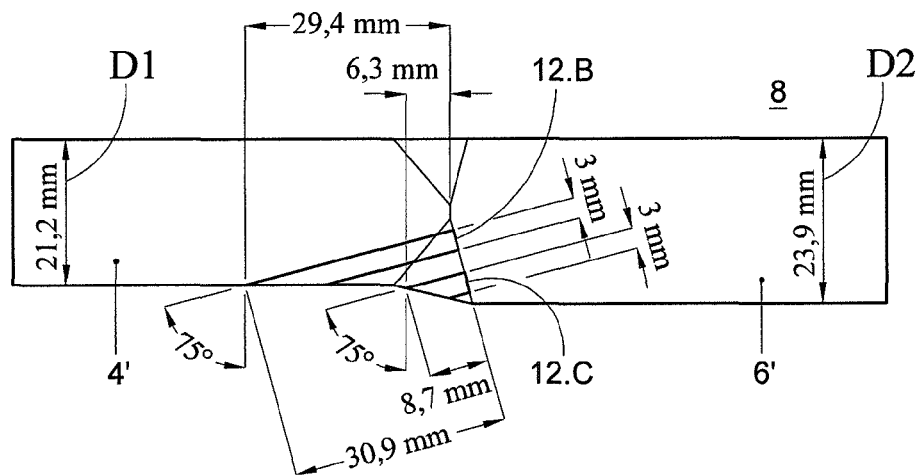
Fig. 3.3

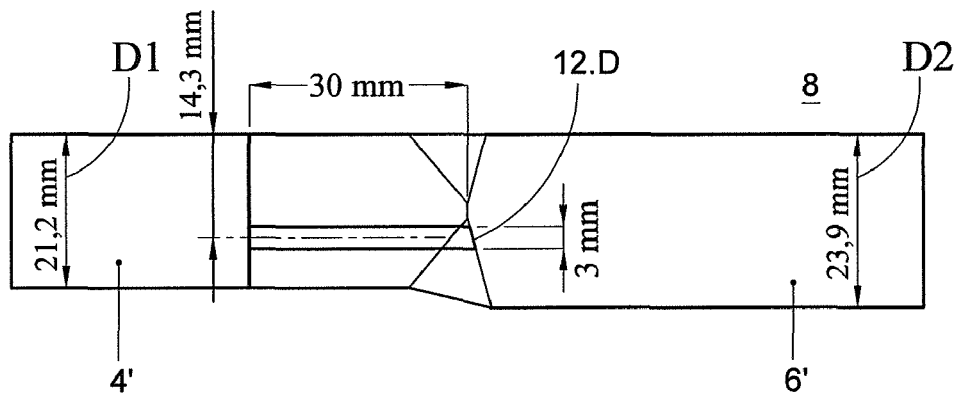
Fig. 3.4
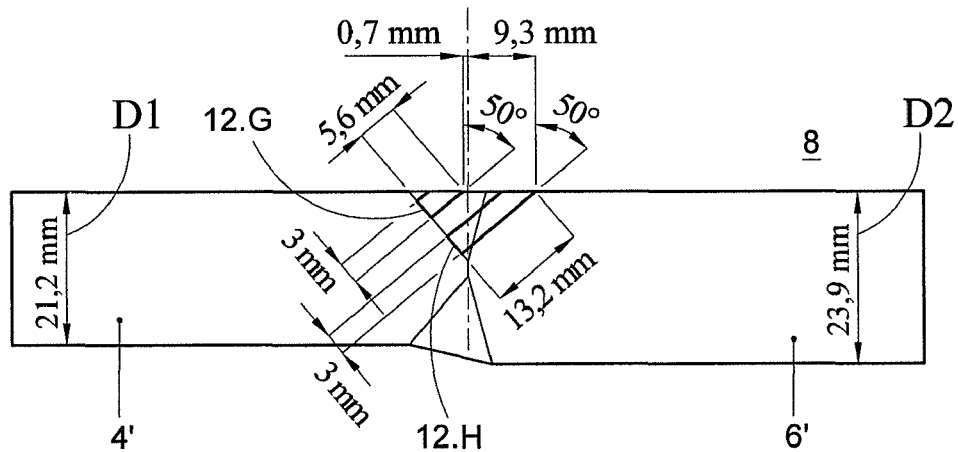
Fig. 3.5
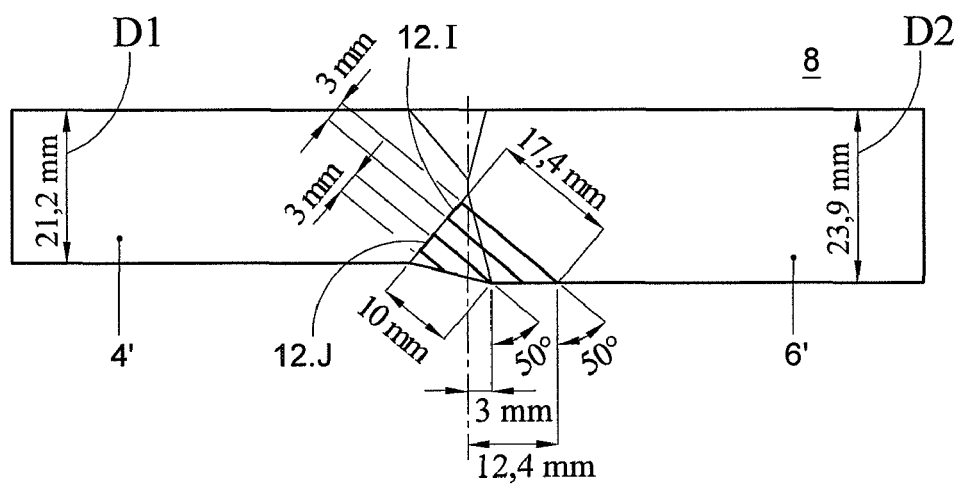
Fig. 3.6

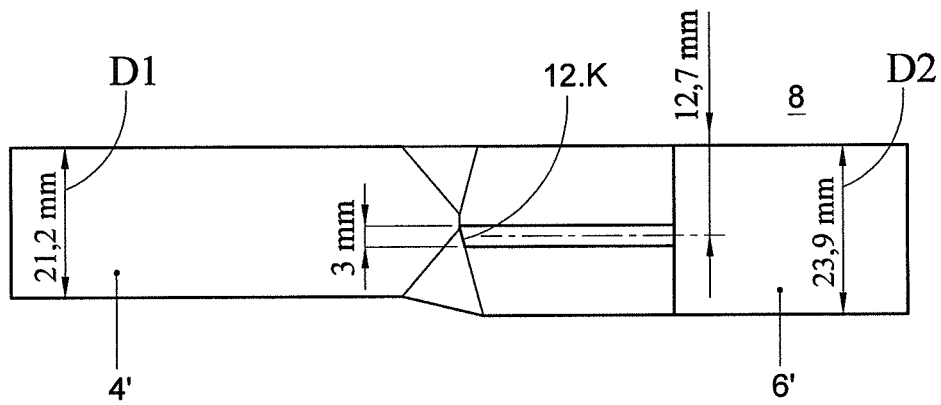
Fig. 3.7
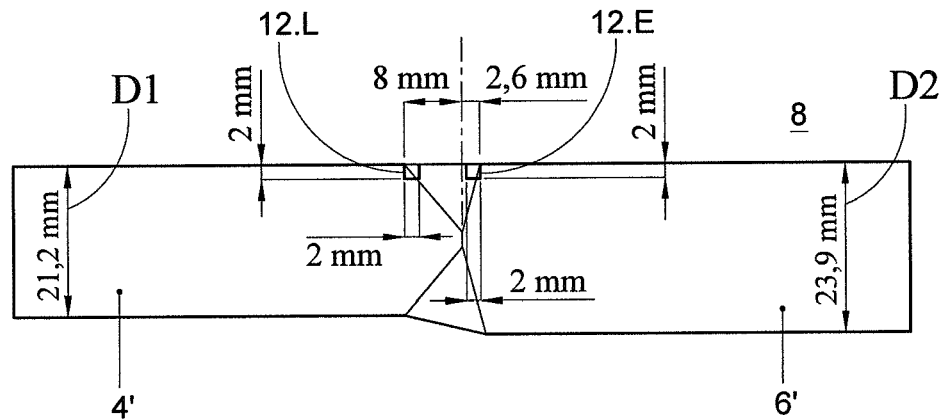
Fig. 3.8
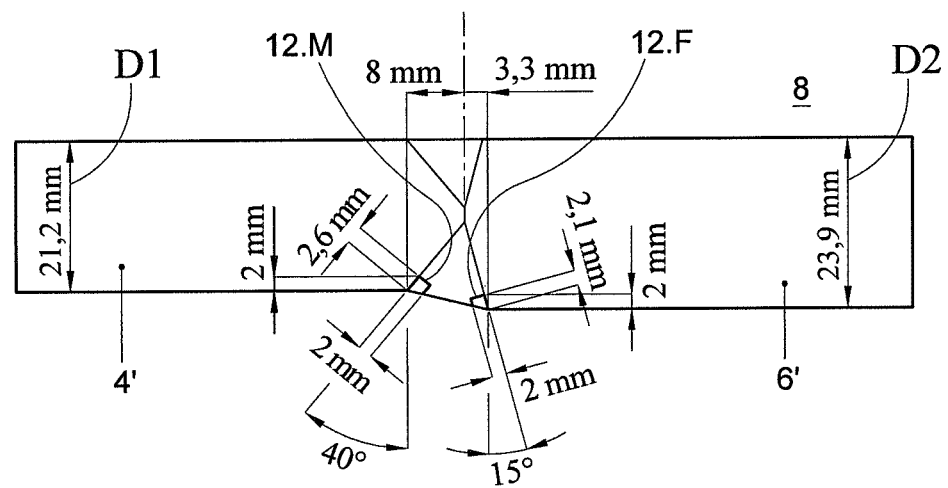
Fig. 3.9

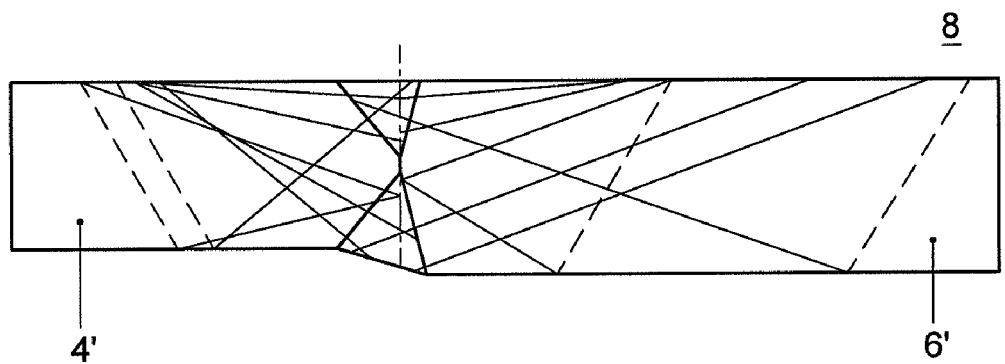
Fig. 5
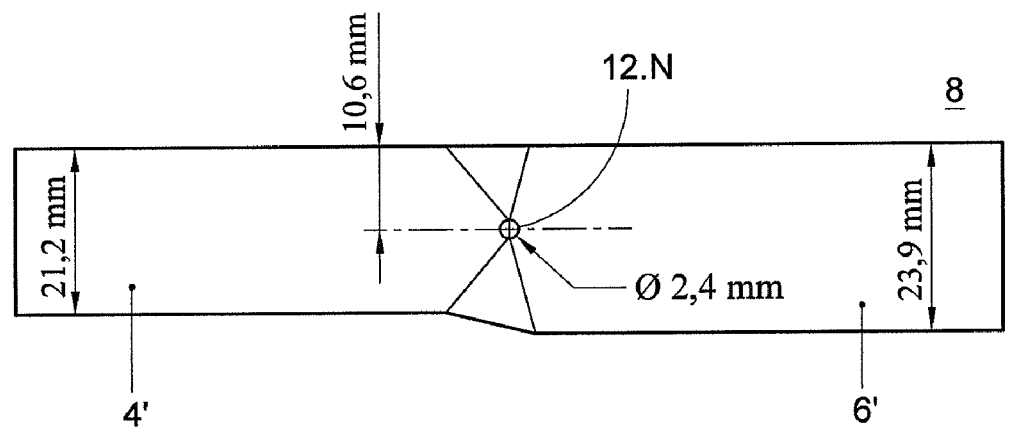
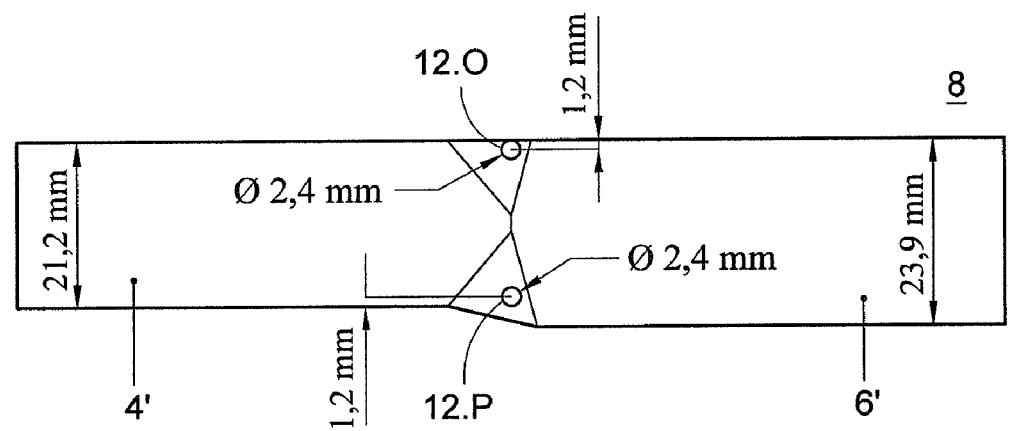
Fig. 6

METHOD FOR CONFIGURING AN ARRAY OF TRANSDUCERS IN AN ULTRASONIC TEST APPARATUS

This is a national stage of PCT/NL2007/050612 filed Dec. 3, 2007 and published in English, claiming benefit of U.S. provisional application No. 60/861,964, filed Dec. 1, 2006.

The present invention relates to a method for configuring an array of transducers in an ultrasonic test apparatus for detecting flaws in coarse-grained welds with anisotropic behavior for ultrasound propagation (for instance austenitic or duplex steel welds), said welds connecting the edges of metal bodies such as plates or pipelines.

It is known that the ultrasonic examination of anisotropic, coarse-grained materials such as austenitic welds gives rise to increased noise, scatter and attenuation of ultrasonic waves when conventional shear wave transducers are used. Therefore, modified ultrasonic techniques are commonly used for this purpose, which use longitudinal rather than conventional shear waves. These transducers are fitted with two crystals rather than one (the functions of transmitter and receiver have been separated). They are indicated with the term TRL (Transmitter-Receiver Longitudinal) transducers.

These techniques have been successfully used for inspection of this type of materials, primarily welds, since 1970, both manually (whereby the transducers are manually scanned) and automated (whereby multiple transducers are mounted in a mechanical device to scan along the weld and data acquisition is done by a computer or similar recording device). Successful automated ultrasonic examinations of austenitic welds using multiple transducers have been published already in 1976 by RTD. Since that time, RTD has been manufacturing and selling TRL transducers for mechanized testing of austenitic welds.

RTD did a first successful feasibility study of these techniques for LNG tanks in 1981.

Coarse-grained, anisotropic welds such as austenitic welds can be applied between austenitic (non-magnetizable) components such as plates or pipes, but also between ferritic (magnetizable) components. The latter is the case in tanks for storage of Liquefied Natural Gas, where the plates are manufactured out of a high-nickel content (e.g. 9%), ferritic steel alloy and the welds usually have an austenitic structure.

The present invention relates to an improved method for implementing these ultrasonic techniques. In particular the present invention relates to the calibration stage.

The method according to the invention is characterized in that the method comprising the steps of:
(a) providing at least one drawing or design of the bodies including the edges ("bevels") of the bodies before being welded, each of said edges comprising at least one facet and generally a plurality of facets with surfaces which are generally angled relative to each other;
(b) identifying different facets of the geometry of the edges of the bodies;
(c) making at least one drawing or design of a reference plate including a (preferably planar) reflector for at least one of the facets and preferably for each of the facets to be inspected;
(d) selecting the angles of the transducers such that their beams will, wherever possible, reflect perpendicular onto the facets of the edges of the bodies;
(e) selecting the positions of the transducers according to the geometry of the edges ("bevels") of the bodies;
(f) providing a reference plate including the reflectors as determined in step (c);
(g) mounting the transducers to a scanning mechanism in accordance with the selections made in step (d) and (e);
(h) connecting the transducers to at least one control unit for transmitting ultrasound and receiving echo signals by means of the transducers and subsequently calibrating by means of the at least one control unit and the reference plate the positions of the transducers relative to the scanning mechanism and calibrating gain and gate settings of the at least one control unit by means of the reference plate wherein step (h) is carried out after step (g) while the transducers are mounted to the scanning mechanism.

An example according to the invention for the inspection of an LNG tank is provided with reference to the drawings wherein.

FIG. 3.1 shows an example of a horizontal weld wherein facets have been identified;

FIG. 3.2 shows a planar reference reflector 12.A in a part of the bevel as shown in FIG. 3.1;

FIG. 3.3 shows planar reference reflectors 12.B and 12.C in parts of the bevel as shown in FIG. 3.1

FIG. 3.4 shows a planar reference reflector 12.D in a part of the bevel as shown in FIG. 3.1;

FIG. 3.5 shows planar reference reflectors 12.G and 12.H in parts of the bevel as shown in FIG. 3.1

FIG. 3.6 shows planar reference reflectors 12.I and 12.J parts of the bevel as shown in FIG. 3.1;

FIG. 3.7 shows a planar reference reflector 12.K in a part of the bevel as shown in FIG. 3.1

FIG. 3.8 shows planar reference reflectors 12.E and 12.L in part of the bevel as shown in FIG. 3.1;

FIG. 3.9 shows planar reference reflectors 12.F and 12.M in apart of the bevel as shown in FIG. 3.1

Figure 4:
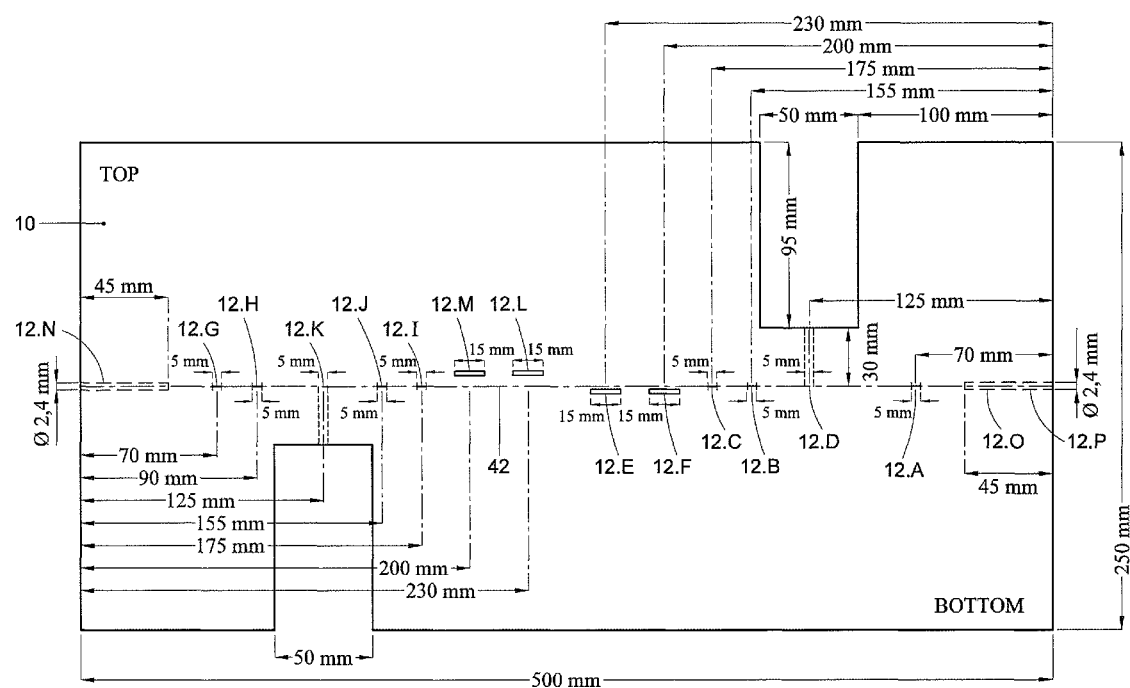

FIG. 4 shows an example of a reference plate drawing including the reference reflectors 12.A-12.M as identified by means of FIGS. 3.1-3.9;

FIG. 5 shows an example of a scan plan for the weld according to FIG. 3.1, showing beams and weld coverage;

FIG. 6 shows side drilled holes to check that gates reach to the weld center for the weld according to FIG. 3.1.

Figure 7:
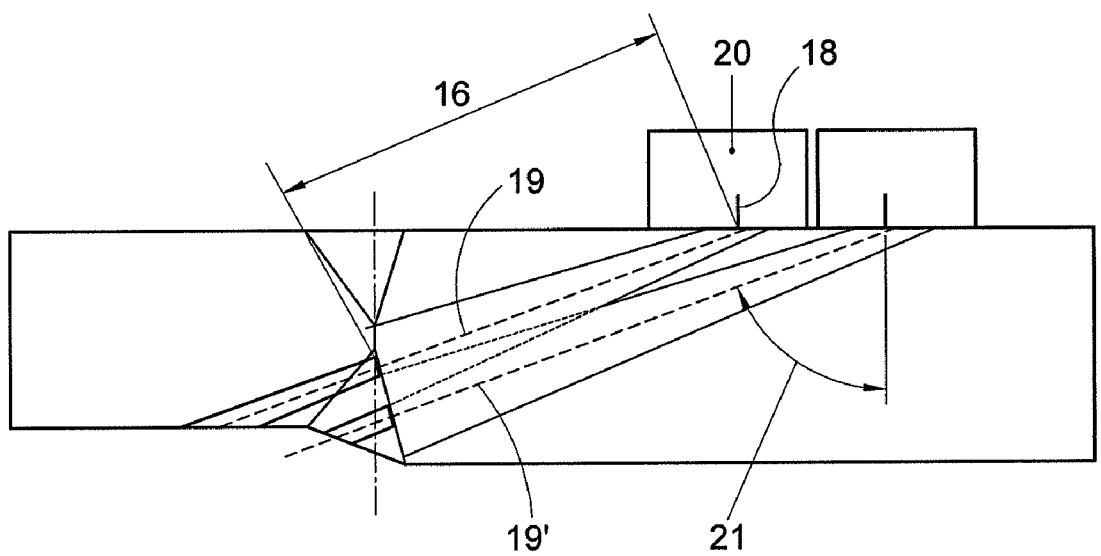

FIG. 7 shows how the focal distance and the sound exit point of a probe are derived from a drawing for the weld according to FIG. 3.1.

Figure 8A:
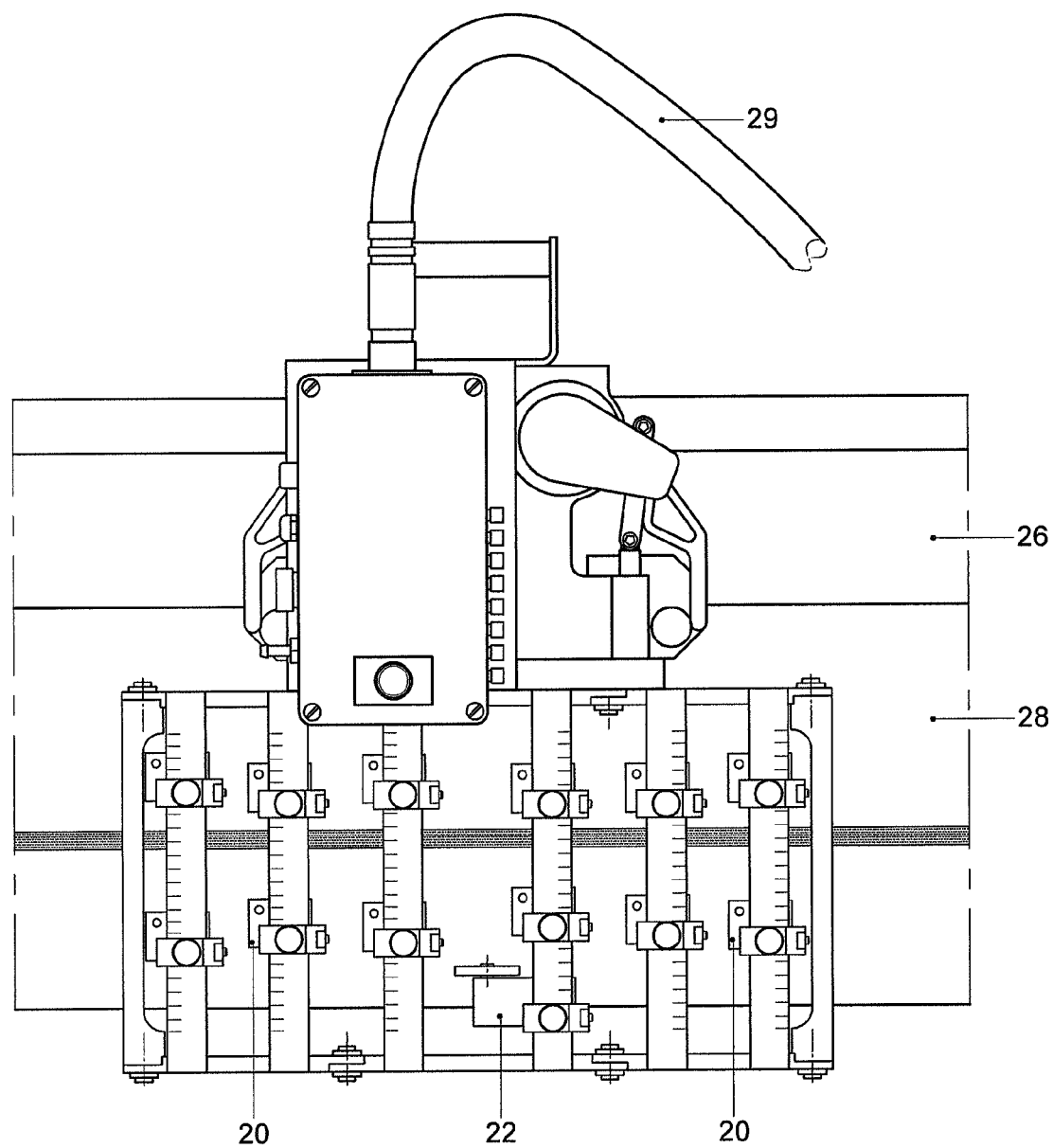
Figure 8B:
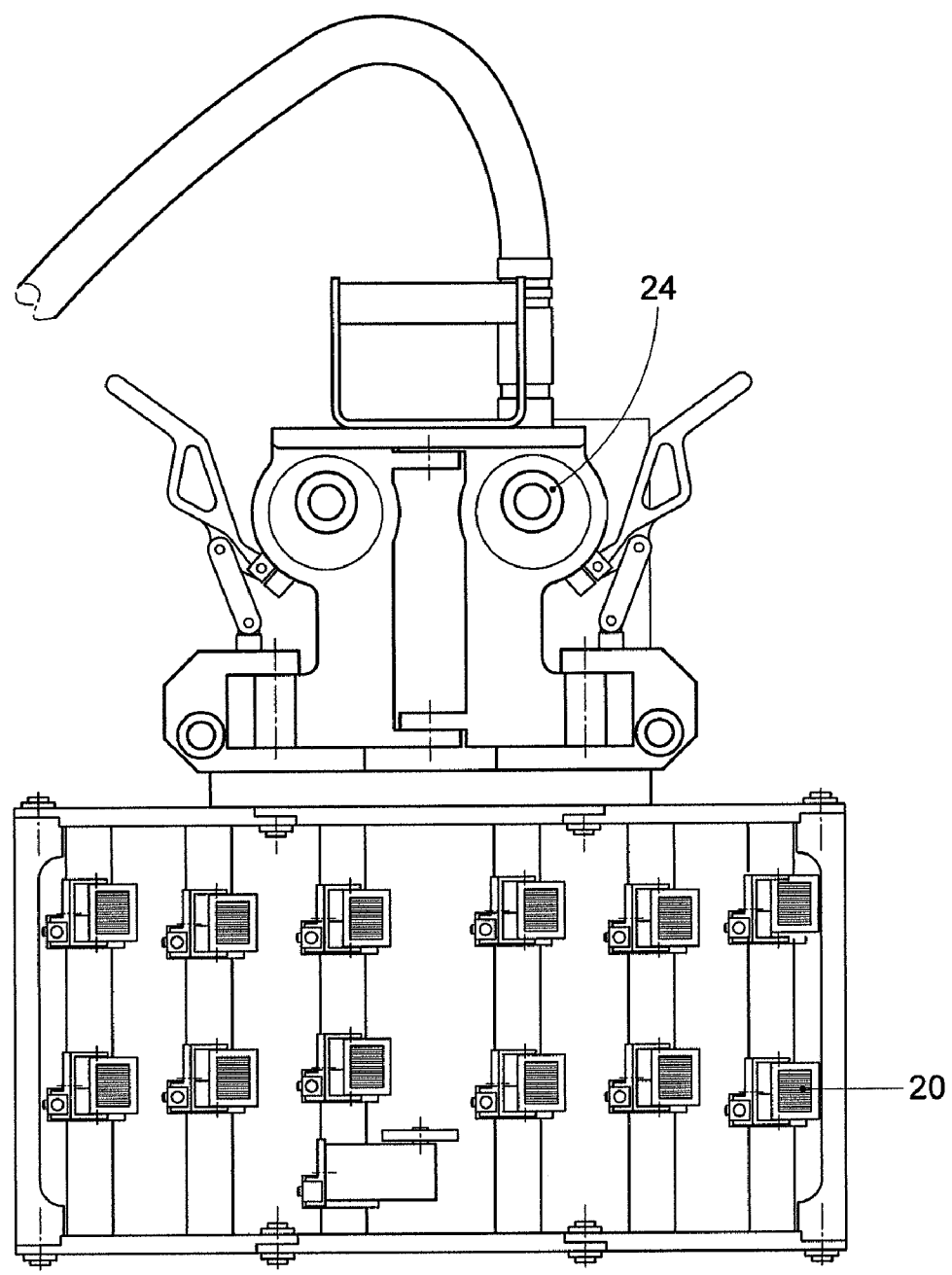
Figure 9:
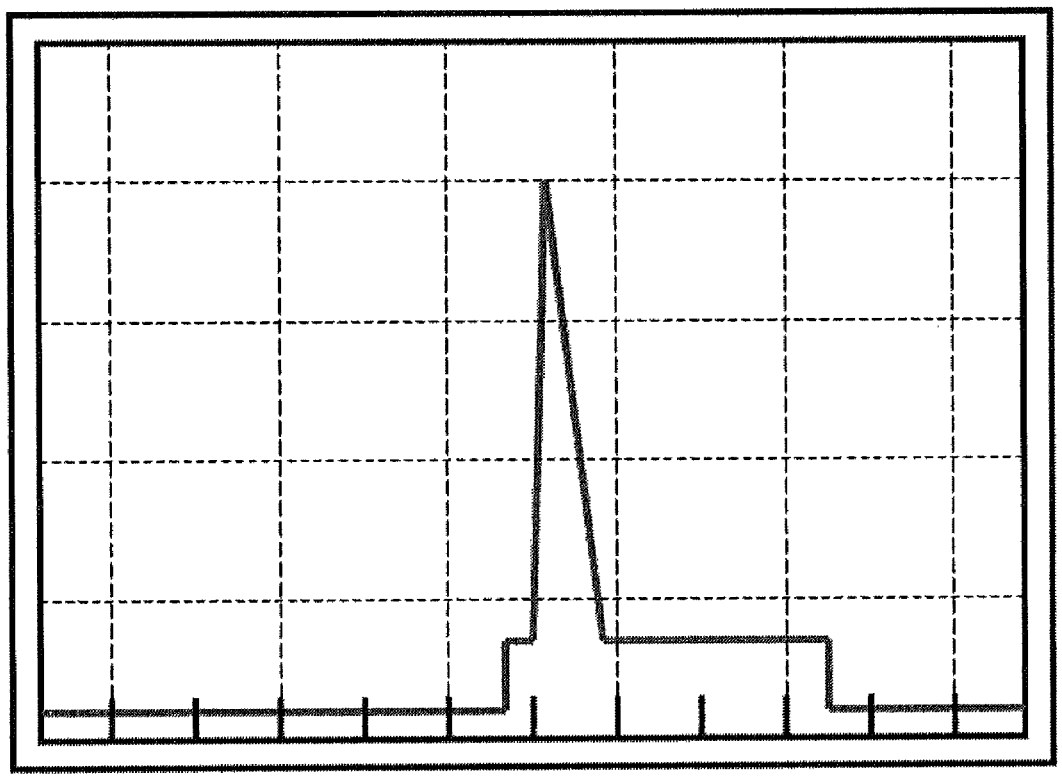

FIG. 8*a* shows a scanning mechanism from a first direction attached to a body holding a reference plate;

FIG. 8*b* shows the scanner of FIG. 8*a* from second direction which is opposite to the first direction;

FIG. 9 shows an example of a display of an ultrasonic signal.

INFORMATION PROVIDED

Figure 1:
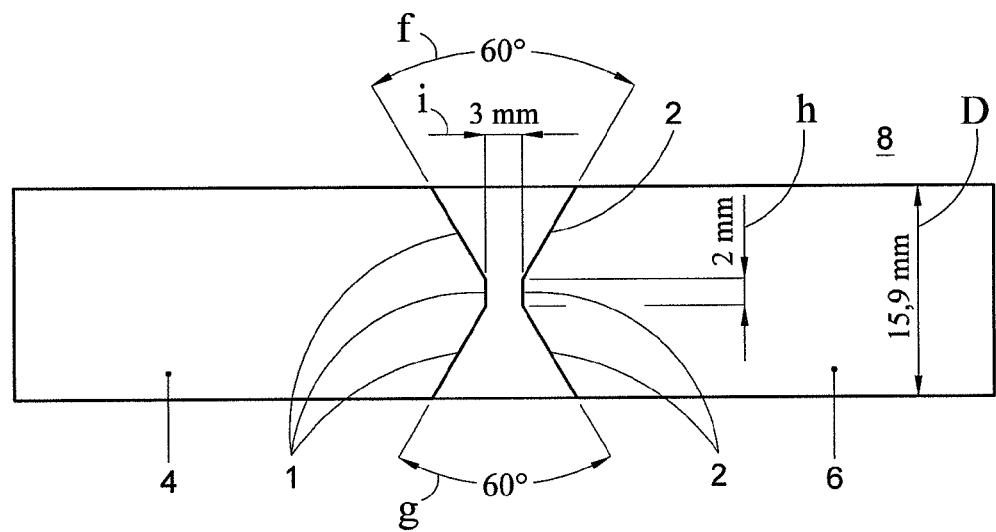
FIG. 1 shows an example of a vertical weld in an LNG tank wherein each edge of the plates comprises three facets which are angled relative to each other.

Information is provided which includes detailed drawings of the shape of the outer surfaces including edges 1, 2 of plates 4, 6 (bevels) before being welded. These plates form for instance part of the wall of an LNG tank before being welded. An example of a detail of such a drawing of a vertical weld is shown in FIG. 1. The inside of the tank has reference number 8.

The drawings show, for each weld to be examined, the wall thickness D, the angles f, g under which the weld preparation surfaces ("weld bevels") are machined and other dimensions h, i as indicated in the example. The drawing thus shows the configuration of the weld bevels as it is before welding, because this is the location where potential lack of fusion defects are likely to occur. Hence the drawing shows the edges of the plated before being welded together. These edges form the bevels of the plates. By the manufacturer, these drawings are used for manufacture of the tank (to machine the plate ends in the correct shape and to develop the welding procedure). In the present example these drawings are used to design the ultrasonic test setup, to design a scan plan and to manufacture reference blocks, to be discussed later in this document.

The weld details are copied in an AutoCAD system or similar software systems.

The example in FIG. 1 is valid for a vertical weld in an LNG tank.

Figure 2:
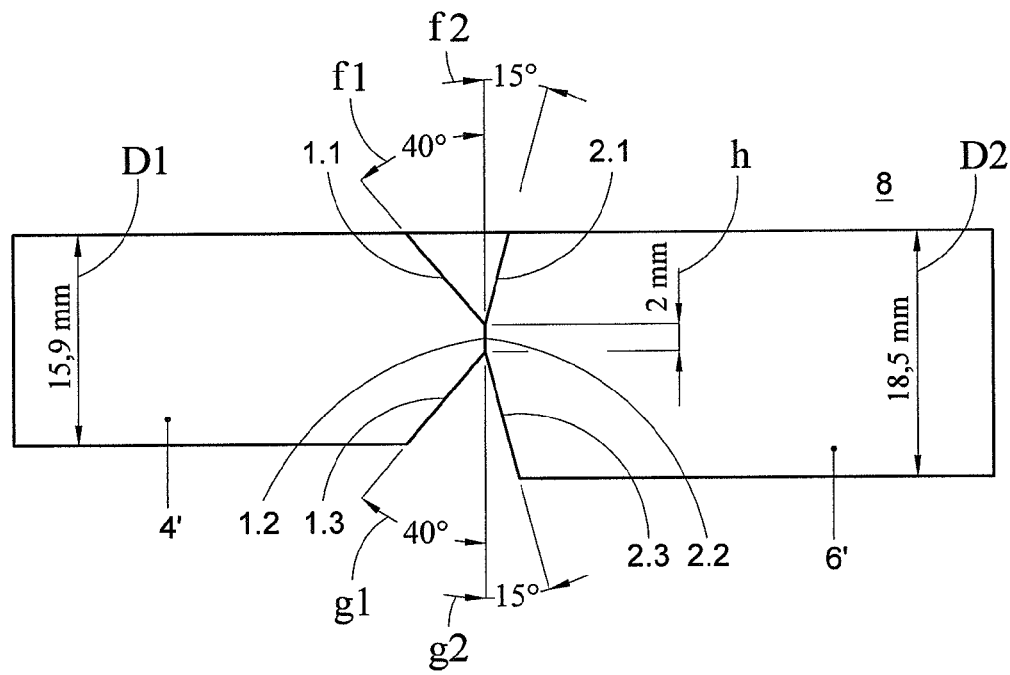
FIG. 2 shows an example of a horizontal weld in an LNG tank wherein each edge of the plates comprises three facets which are angled relative to each other.

FIG. 2 shows a horizontal weld between plates 4', 6', horizontal welds can be asymmetric because a tank can be composed from sections (rings) of different thicknesses. The thickness of plate 4' is D1 and the thickness of plate 6' is D2.

In this example a Code or Standard that the weld examination has to comply with is also supplied. A code commonly used for storage tanks is the API 620 (latest and current edition is the $10^{th}$ edition, February 2002, with addendum June 2004). This edition of the code allows for the use of ultrasonic examination in lieu of radiographic testing, and requires that the examination is done with an automated, computer-based system and that defect sizing (determination of defect height in through-thickness direction and defect length in welding direction) is performed. The acceptance criteria for weld imperfections as mentioned by the Code are based on flaw length as a function of flaw height, as measured by the system during weld examination.

The approach has been designed to be able to comply to code requirements such as, for example, the API 620 for storage tanks.

It is chosen to perform defect sizing with the automated system, not by additional manual techniques. This is the basis of the design of the ultrasonic setup.

Reference Reflectors Based on Weld Bevel Shape

The following starting points are used for the design of the ultrasonic concept:

- On the basis of the drawing, different sections (facets) of the geometry of the edges of the plates are identified. As an example: the weld bevel at the left side of the weld in FIG. 2 has, from top to bottom, an inclined part (facet) 1.1 under 40° (angle f1), then a small so called "nose" (facet) 1.2 under 90° and then a second inclined part (facet) 1.3 under 40° (angle g1). Lack of fusion defects along these bevel parts, together with (near) vertical "solidification cracks" (which can occur during welding) have the highest sizing priority, and this is what the ultrasonic system design primarily focuses on. A similar approach is chosen for the right side of the weld, where the inclination angles f2, g2 are 15°. Hence facets 2.1, 2.2 and 2.3 are identified. In vertical welds, which are symmetric, the approaches for left and right side are identical.
- In the drawing, reference reflectors 12 are drawn for the different expected flaw positions. This can be holes, notches etc. An overall drawing of a reference plate that includes all these reference reflectors is then made. The material for the reference plate is derived from the client, and contains a representative austenitic weld, similar to those present in the client's installation.
- Every part (facet) of the "bevel" will have at least one planar reflector in the reference plate. For this purpose, flat bottomed holes or elongated notches with a flat bottom are typically used. The reflecting part (e.g. the bottom of the hole or notch) is situated in the plane of the bevel.
- The angles of the probes are chosen in such a way that the ultrasonic beam will, wherever possible, reflect perpendicularly onto the local bevel part. This, in combination with the concept of planar reference reflectors, will allow for height sizing of planar weld bevel defects by using a relationship between the dimension of the reflector in the drawing plane and the echo amplitude of the ultrasonic signal. This is possible by using perpendicular incidence on the bevel (by using a potential bevel defect as a mirror for ultrasonic waves). The relationship between defect height and amplitude is established by the use of so-called "sizing curves" which are specific for the frequencies, angles and beam widths of the probes used. Such sizing curves are derived from computer simulations and are validated by experiments. They are subsequently implemented in the inspection software, to enable (during weld examination) direct conversion of echo amplitudes to estimated flaw sizes. These flaw sizes are then compared to the Code's acceptance criteria for weld imperfections. Although the accuracy of height sizing in austenitic welds is limited, because of the coarse-grained, anisotropic weld structure, it has been proven to be good enough to meet the Code's requirements when this approach is used. Therefore, table U1 in the code can be used.
- The reference plate 10 is obtained based on the drawings wherein for each facet 1.*i* (i=1, 2, . . . ), 2.*j* (j=1, 2, . . . ) at least one reference reflector 12.*k* (k=A, B, C, . . . ) is inserted in the reference plate. After the reference reflectors 12.*k* example 13 reference reflectors are selected which are indicated as A-M) for each part of the bevel have been inserted in the reference plate 10, together with other reflectors to be described later in this document, the plate will be used for calibration of the ultrasonic system.

FIG. 3.1 shows the weld preparation of a horizontal weld such as discussed with reference to FIG. 2, FIG. 3.2 shows the reference reflector 12.A, FIG. 3.3 the reference reflectors 12.B and 12.C etc. . . . . . Based on the drawing of FIG. 3.1 different sections (facets) of the geometry of the edges of the plates are identified. The outcome is in this example the same as discussed above for FIG. 2. The weld bevel at the left side of the weld in FIG. 3.1 has, from top to bottom, an inclined part (facet) 1.1 under 40° (angle f1), then a small so called "nose" (facet) 1.2 under 90° and then a second inclined part (facet) 1.3 under 40° (angle g1). Lack of fusion defects along these bevel parts, together with (near) vertical "solidification cracks" (which can occur during welding) have the highest sizing priority, and this is what the ultrasonic system design primarily focuses on. A similar approach is chosen for the right side of the weld, where the inclination angles f2, g2 are 15°. Hence facets 2.1, 2.2 and 2.3 are identified. Based on FIG. 3.1 in the drawings 3.2-3.9 reference reflectors 12.*k* (k=A, B, - - - I) are drawn for the different expected flaw positions. As an example, reflector 12.A is a planar reflector in the upper right 15° part of the bevel; see FIG. 3.2., Note that the flat bottoms of the planar reflectors 12.A, 12.B, 12.C, 12.G, 12.H, 12.I and 12.J are in the bevel's plane. In this way, they represent typical lack of fusion defects that can occur in this type of welds. A similar approach is used for the other parts of the bevel.

When thicker walls have to be inspected, more reference reflectors per bevel part are sometimes required to ascertain perpendicular incidence and sufficient beam overlap.

As a reference for detection and sizing of vertical defects in the weld's center (such as "solidification cracks"), a horizontally machined reflector such as 12.D and 12.K (with their bottoms vertical) are used. In this way, a vertical reflector in the center of the weld is obtained. Examples are shown in FIGS. 3.4 and 3.7 (Note that the plates shown in the figures are shown as examples and are derived from reference plates having different thicknesses, for different parts of the tank). The type of defects that this reflector simulates (e.g. solidification cracks) is detected and sized with the aid of the so-called Round Trip Tandem technique, whereby longitudinal waves are emitted by the (transmitting crystal of the) transducer and are reflected by the defect; at the back wall, the waves are converted into shear waves and received by the (receiving crystal of the) transducer.

In order to be able to machine this hole, the reference plate 10 has to have a special shape. An example of a reference plate drawing for a horizontal weld is shown in FIG. 4. The view on the reference plate is from inside the tank. The reference reflectors 12.A-12.M as derived form FIGS. 3.1-3.9 are indicated. Also three other reflectors 12.N, 12.O and 12.P are shown. These reflectors will be described later.

In FIG. 4 "Top" indicates the plate above the weld and "Bottom" the plate below the weld. These plates can have different thicknesses. Reference plates for vertical welds have a similar lay-out. For a complete tank, for instance 3 reference plates are needed for vertical welds and 3 for horizontal welds, to cover the entire thickness range of a tank (typically between 10 and 25 mm).

The near surface areas of the weld are inspected by means of so-called creeping wave transducers. These are transducers of which the beam runs more or less parallel to the surface. In this way, surface imperfections can be detected.

In order to be able to calibrate the creeping wave transducers on representative surface reflectors (set the gain), surface notches 12.E, 12.L, 12.F and 12.M are typically machined in the reference plate 10, as seen in FIGS. 3.8 and 3.9. This type of notches is usually machined as a rectangular saw cut or EDM notch, with its main dimension (length) perpendicular to the drawing plane.

Creeping wave transducers also have a beam lobe under an angle, this means that they inspect more than just the surface area.

Scan Plan

In compliance with the Code, a so-called "scan plan" has to be made. This scan plan includes the beam directions as required by the code. FIG. 5 shows an example of a scan plan for a horizontal weld described above. The longitudinal wave beams are indicated by solid lines, shear wave beams are indicated by dotted lines. The scan plan shown in FIG. 5 is an example for a horizontal weld as shown in FIGS. 3.1-3.9. It also shows weld coverage by means of the beams.

Transducer Selection

TRL transducers equipped for automated UT are used, and by means of a drawing the focal distance 16 of each transducer 20 is selected in such a way that maximum sensitivity is achieved at the location of the relevant reference reflector for that particular transducer. An example of such a drawing is shown in FIG. 7. The focal distance is chosen equal to the distance between the sound exit point 18 of the probe and the reflector. This ascertains maximum signal strength at the location of the reflector. Laws of physics indicate that larger focal distance, maintaining a reasonable beam width, requires larger crystals, thus a larger transducer. Since the location of the sound exit point 18 of the transducer is more or less dictated by the shape of the weld, transducers can not be very large. From experience it can be said that the beam width 19 (see FIG. 7) will always be large enough when practical transducer sizes are used. Therefore, the requirement of having adequate beam overlap 19' will automatically be met, because the beams of all transducers together will cover the entire weld volume. At a later stage, beam overlap will be confirmed as a part of the calibration procedure.

The probe angle 21 is carefully selected for perpendicular incidence on the relevant reflector on the bevel.

In cases where perpendicular incidence on a reference reflector requires reflection against the back wall, shear wave beams will be used as a primary beam, these are then mode converted upon reflection to generate the required longitudinal beam for perpendicular incidence. This is called "shear-longitudinal reflection". The primary shear wave beams are shown as dotted lines in FIG. 5. This is done because the use of longitudinal-longitudinal reflection against the back wall is very inefficient.

In cases where even said shear-longitudinal reflection does not generate sufficient signal to noise ratio, shear-shear reflection at the back wall can be used as an alternative for hitting lack of fusion defects perpendicularly. This is only possible if the ultrasonic waves do not need to penetrate through coarse-grained, anisotropic weld material. It can therefore only be used for bevel defects. If shear-shear reflection is used, it has always to be supplemented by longitudinal waves to ascertain penetration through the weld material as well.

The ultrasonic frequency of the probes is, for instance in the case of an LNG tank, usually around 2 MHz. This value is not only derived from experience, but also recommended in literature (IIW Handbook, 1986).

The scanning mechanism is shown in FIGS. 8a and 8b.

The scanning mechanism 22 is in this example capable of taking up a maximum of approx. 12 transducers 20. It is equipped with an encoder 24 (which is required for using it in combination with a computerized data acquisition system). A cable 29 is connected to a signal processing means which is known as such.

The scanning mechanism is running on rails 26, which are mounted to the tank 28 with the aid of suction cups 30. Although the plate material of LNG tank is magnetizable, magnets are not used because one may wish not to induce remanent magnetism to the tank. This is because this could impede possible later repair welding (the welding arc might be deflected as a result of the remanent magnetism, which could induce lack of fusion defects). Also other guiding systems can be used, provided they give accurate guiding to the scanning mechanism.

The scanner enables to mount transducers on either side of the weld, in order to examine the weld from both sides. In case of an asymmetric weld, the transducer angles etc. at both sides may be different because they have to be optimized to different bevel shapes.

Calibration

For a complete tank, typically 6 reference plates are needed (three for vertical, three for horizontal welds), to cover the complete plate thickness range of approx. 10 to 25 mm.

As soon as the transducers and reference plates 10 are available, the transducers are mounted in the scanning mechanism. Preliminary transducer positions are estimated on the basis of the scan plan.

The reference plate is mounted in a large dummy plate, which allows for rails to be mounted. In this way, the entire scanning mechanism with the transducers is placed over the reference plate (see FIG. 8) and forms a scanner 21.

For calibration of the system (setting the exact position of the transducers relative to the scanner and setting of gain and gate for each individual transducer), the scanner is moved along the rails until one of the transducers 20 is positioned over its relevant reference reflector 12.A-12.M. The transducer is then, prior to fixing it in its optimized position, moved in its holder 32 in order to optimize the reflection from the relevant reflector. To watch the reflections on a screen, a first control unit 34 in the form of a standard single or multi-channel ultrasonic flaw detector is used. As soon as the maximum amplitude has been reached, the transducer holder 32 is tightened and the transducer 20 is correctly positioned in the scanning mechanism. The same procedure is followed for the other transducers as well. After all transducers have been fixed, all transducers are connected to the computerized data acquisition system 34.

After this procedure has been completed, the computer 34 is programmed in such a way that each probe is assigned to a certain sequence of the ultrasonic equipment. This means that for instance in sequence 1 a wave is fired by probe 1 (which can be the probe indicated as 20), which will reflect to a reflector and return in probe 1. After that, and not earlier, probe 2 is fired in sequence 2 and the same repeats itself. Then sequence no. 3, etc. This is the principle of multi-channel automated systems. This principle makes sure that not more than one wave front is underway at the same time, thus avoiding conflicts and misinterpretations. Each sequence comprises a time gate. This time gate is set as follows.

The scanner 21 is repositioned a number of times along the rails to place each of the probes over its relevant reflector. Each individual gain is then adjusted in such a way that an amplitude of 80% of the full screen height is seen on the screen of the data acquisition system. The gate start is set in such a way that it includes the reflectors' echo, i.e. starts just before the echo appears on the screen of the computer (this is just left of the echo on the time base; see FIG. 9. Then the gate start is modified (moved to the left on the time base) in such a way that there is a certain space between the gate start and the echo. This is to include the heat affected zone in the gate according to code requirements.

Gate end is set in such a way that it is ascertained that the gate reaches until the weld center line. To this end, some additional holes have been drilled in the weld center 42 of the reference plate 10 to provide reflectors 12.N. 12.O and 12.P respectively, the echo of which must just be included in the gate.

FIG. 6 shows in a drawing a set of such reflectors 12.N, 12.O, 12.P as an example (diameter for instance 2.4 mm). These reflectors 12.N, 12.o, 12.P are only used for gate setting as a check on weld coverage, not for gain setting.

After having completed the settings of all transducers, the scanning mechanism is scanned over the reference plate. All signals are now captured by the data acquisition system. This is called the "dynamic calibration check". Echo amplitudes must now be at 80% of the full screen height, within certain tolerances. If this is the case, the system has been properly calibrated for the weld inspection job. This also checks that the system is capable of finding the relevant planar flaws, because these are also the reference reflectors on which the system has been calibrated.

Written Procedure

A written procedure is written for each job, describing how all the code requirements are implemented in the ultrasonic examination procedure. This written procedure also describes regular calibration checks: during the examination of the welds in the tank, the "dynamic" calibration check is repeated with certain intervals, according to the written procedure, along with the other details of the examination.

Weld Examination

After having completed the above described "job preparation" procedure, the welds of the tanks will be inspected.

A similar procedure can be followed for the inspection of other type of welds, for example welds for pipelines.

Instead of at least one drawing of the bodies a design which comprises for example a data of the geometry of the bodies may be used in a computer without drawings being shown on a screen or being printed. The computer may for example perform pattern recognitions for recognizing the facets of the edges and calculating based thereon the positions and angles of the transducers, the focal length of the transducers, the beam direction of the transducers, the design of the reference plate and its planar reflectors, etc.

The procedure is most suitable for being used for coarse-grained welds with anisotropic behavior for ultrasound propagation such as for instance austenitic or duplex welds.

The invention is not limited to the example provided above. Instead of using a drawing of the plates and the corresponding bevel a model of the plates and corresponding bevel may be used for determining the reference reflectors, the scan plan and selecting the transducers. This process may also be performed by a computer program running on a computer wherein the computer calculates the reference reflectors, the scan plan and selects the transducers based on dimensions of the plates and the corresponding bevels.

The invention claimed is:

1. A method for configuring an array of transducers in an ultrasonic test apparatus for detecting flaws in coarse-grained welds with anisotropic behavior for ultrasound propagation, said welds connecting the edges of metal bodies, the method comprising the steps of:
   (a) providing at least one drawing or design of the bodies including the edges of the bodies before being welded, each of said edges comprising at least one facet and generally a plurality of facets with surfaces which are generally angled relative to each other;
   (b) identifying different facets of the geometry of the edges of the bodies;
   (c) making at least one drawing or design of a reference plate including a reflector for at least one of the facets and preferably for each of the facets to be inspected;
   (d) selecting the angles of the transducers such that their beams will reflect perpendicular onto the facets of the edges of the bodies;
   (e) selecting the positions of the transducers according to the geometry of the edges of the bodies;
   (f) providing a reference plate including the reflectors as determined in step (c);
   (g) mounting the transducers to a scanning mechanism in accordance with the selections made in step (d) and (e);
   (h) connecting the transducers to at least one control unit for transmitting ultrasound and receiving echo signals by means of the transducers and subsequently calibrating by means of the at least one control unit and the reference plate the positions of the transducers relative to the scanning mechanism and calibrating gain and gate settings of the at least one control unit by means of the reference plate wherein step (h) is carried out after step (g) while the transducers are mounted to the scanning mechanism.

2. Method according to claim 1, characterized in that step (d) and (e) are carried out by means of the drawing or design of the bodies.

3. Method according to claim 1, characterized in that step (c) is carried out by means of the drawing or design of the bodies.

4. Method according to claim 1, characterized in that, in step (h) the transducers are connected to a first control unit for calibrating the positions of the transducers relative to the scanning mechanism and in that, in step (h) the transducers are connected to a second control unit in the form of a data acquisition system for setting the gain and gate settings of the data acquisition system.

5. The method according to claim 1, characterized in that prior to step (h) on the basis of the drawing or design of the bodies the focal distances of the individual transducers are selected such that, for each individual transducer, the maximum sensitivity is achieved at the locations of the relevant reflector.

6. The method according to claim 1, characterized in that in step (h) the scanning mechanism is moved along the reference plate for positioning the transducers over the reflectors for calibrating the position of the transducers.

7. The method according to claim 1, characterized in that in step (h) the scanning mechanism is moved along the reference plate for positioning the transducers over the reflectors for calibrating the gain and gate settings.

8. The method according to claim 1, characterized in that in a step (i) the at least one control unit is programmed for activating the transducers in accordance to at least one certain sequence.

9. The method according to claim 4, characterized in that in a step (i) the data acquisition system is programmed for activating the transducers in accordance to at least one sequence.

10. The method according to claim 1, characterized in that in step (h) the positions of the transducers in the scanning mechanism are calibrated by optimizing received echo amplitudes of the relevant reference reflector.

11. The method according to claim 10, characterized in that the positions of the transducers in the scanning mechanism are calibrated before the gain and the gate settings are calibrated.

12. The method according to claim 8, characterized in that the step (i) is carried out before the gain and the gate settings are calibrated in step (h).

13. The method according to claim 8, characterized in that step (i) is carried out after the position of the transducers in the scanning mechanism is calibrated.

14. The method according to claim 1, characterized in that after step (h) a test scan is performed on the reference plate.

15. The method according to claim 8, characterized in that the at least one sequence is set with one gate setting.

16. The method according to claim 1, characterized in that in step (h) by means of the reference plate a gate start and a gate end of a gate setting are set such the gate includes an echo of the relevant reflector.

17. The method according to claim 16, characterized in that in step (h) by means of the reference plate a gate start of the gate setting is set such the gate includes reflections from a heat affected zone.

18. The method according to claim 16, characterized in that a gate end of the gate setting is set by means of the reference plate such that the gate includes a weld centre line of the weld.

19. The method according to claim 17, characterized in that the reference plate is provided with some holes at a centre line of the weld for setting the gate end.

20. The method according to claim 1, characterized in that in step (e) at least one transducer is selected such that, in use, shear wave beams will be used as a primary beam, which beams are then mode converted upon reflection to a wall of the metal bodies to generate the required longitudinal beam for perpendicular incidence.

21. The method according to claim 1, characterized in that in step (e) at least one transducer is selected such that, in use, shear wave beams will be used as a primary beam, which beams are then reflected to a wall of the metal bodies to generate a shear wave beam for perpendicular incidence.

* * * * *